(12) United States Patent
Laukhina et al.

(10) Patent No.: US 8,343,436 B2
(45) Date of Patent: Jan. 1, 2013

(54) ORGANIC SENSOR DEVICE AND ITS APPLICATIONS

(75) Inventors: Elena Laukhina, Bellaterra (ES); Marta Mas Torrent, Bellaterra (ES); Concepcio Rovira Angulo, Bellaterra (ES); Jaume Veclana Miro, Bellaterra (ES); Vladimir Laukhin, Bellaterra (ES)

(73) Assignees: Consejo Superior de Investigaciones Cientificas, Madrid (ES); Institucio Catalana de Recerca I Estudis Avancats, Barcelona (ES)

( * ) Notice: Subject to any disclaimer, the term of this patent is extended or adjusted under 35 U.S.C. 154(b) by 539 days.

(21) Appl. No.: 12/515,009

(22) PCT Filed: Nov. 13, 2007

(86) PCT No.: PCT/ES2007/070184
§ 371 (c)(1),
(2), (4) Date: Oct. 2, 2009

(87) PCT Pub. No.: WO2008/059095
PCT Pub. Date: May 22, 2008

(65) Prior Publication Data
US 2010/0028209 A1    Feb. 4, 2010

(30) Foreign Application Priority Data
Nov. 14, 2006   (ES) .................. 200602887

(51) Int. Cl.
*G01N 7/00*    (2006.01)
(52) U.S. Cl. .................. 422/421; 422/68.1; 422/82.12; 422/82.13; 422/83

(58) Field of Classification Search .................. 422/421, 422/68.1, 82.12, 82.13, 83
See application file for complete search history.

(56) References Cited

U.S. PATENT DOCUMENTS 5,386,715 A * 2/1995 Evans et al. .................. 73/31.05
7,811,433 B2 * 10/2010 Manoukian et al. .......... 204/415
(Continued)

FOREIGN PATENT DOCUMENTS
EP      0 109 489 A2    5/1984
(Continued)

OTHER PUBLICATIONS

Clemendot et al., "Evaluation of conducting LB films based on ethylenedithio-tetrathiafulvalene(EDT-TTF) derivatives for phosphine sensing", Sensors and Actuators B, 6 (1992) 197-201.*

(Continued)

*Primary Examiner* — Jill Warden
*Assistant Examiner* — Monique Cole
(74) *Attorney, Agent, or Firm* — K&L Gates LLP

(57) ABSTRACT

The invention is characterized in that it has a layer of organic material sensitive to changes in pressure, voltage, deformation, gases and/or temperature; wherein said organic layer consists of at least one conductive salt or complex including a molecule A and a dopant D, said molecule A being an electron donor or acceptor organic molecule or macromolecule capable of forming a conductive salt or complex, which without doping is not conductive, and with the presence of dopant D becomes a compound that is donor or acceptor of electrons and capable of forming conductive salt or complex with the molecule or macromolecule A; and a base substrate, in close contact with said layer of organic material. The sensor device is useful in molecular electronics or plastic electronics, in particular, in the field of organic sensors.

18 Claims, 8 Drawing Sheets

U.S. PATENT DOCUMENTS

2004/0188682 A1    9/2004    Hirai

FOREIGN PATENT DOCUMENTS

| EP | 1416069 | 5/2004 |
|---|---|---|
| ES | 2272172 | 4/2007 |
| WO | 93/03355 A1 | 2/1993 |
| WO | 2006/057987 A1 | 6/2006 |
| WO | 2007/014975 A1 | 2/2007 |

OTHER PUBLICATIONS

Electrical Conductivities and Superconducting Properties, Chapter 4, 115-179.

Adhikari, B. et al., "Polymers in Sensor Applications", Prog. Polym. Sci. 29, 699-766 (2004).

Kurmoo, M. et al., "Tuning the Carrier concentration in Organic Conductors: Synthesis and physical properties of BEDT-TTF salts with H2PO4- and HPO42-", Synthetic Metals, 70, 795-796 (1995).

Lyubovskii, R.B. et al., "Anomalous Conductivity Dependence of B-(PT)2I3 and B-(PT)2IBr2 (PT=bis (propylenedithio) tetrathiafulvalene) organic conductors under high pressure", Synthetic Metals, 40, 155-160 (1991).

Someya, T. et al. "A large-area, flexible pressure sensor matrix with organic field-effect transistors for artificial skin applications", PNA, 101(27), 9966-9970 (2004).

\* cited by examiner

ORGANIC SENSOR DEVICE AND ITS APPLICATIONS

CROSS REFERENCE TO RELATED APPLICATIONS

This application is a national phase of PCT/ES2007/070184 filed on Nov. 13, 2007 which claims priority to Spanish application No. P200602887 filed on Nov. 14, 2006, the entire disclosures of which are incorporated herein by reference.

BACKGROUND

A sensor has the purpose of providing physical, chemical or biological information on our environment. The materials traditionally used as sensors are based on inorganic compounds, semiconductors, electrolytes, metals and catalytic materials.

Insulating organic and intrinsically conductive polymers have been used in sensor preparation.

For example, intrinsically conductive polymers have been used as a coating material or to encapsulate an electrode and non-conductive polymers are used to immobilise the receptive agents of the device Sensors with organic transistors have also been manufactured, but in order to prepare devices such as these, many different stages are required.

Definition of Terms

Certain terms as used in the specification are intended to refer to the following definition, as detailed below. Where the definition of terms departs from the commonly used meaning of the term, the applicants intend to utilize the definition provided below, unless specifically indicated.

As used herein, the term "sensitive to changes in pressure, tension, deformation, tension, ambient gases and/or temperature" refers to the capacity of the organic material to detect changes in pressure due to a force applied directly to, at least, a part of the surface of the organic material such as a tension, pressure, deformation, shearing or pressure exerted by a fluid, and/or the capacity of the organic material to detect changes in temperature. As used herein, the term "sensory" has also been used with the same meaning.

DETAILED DESCRIPTION OF EXAMPLE EMBODIMENTS

Figure 1:
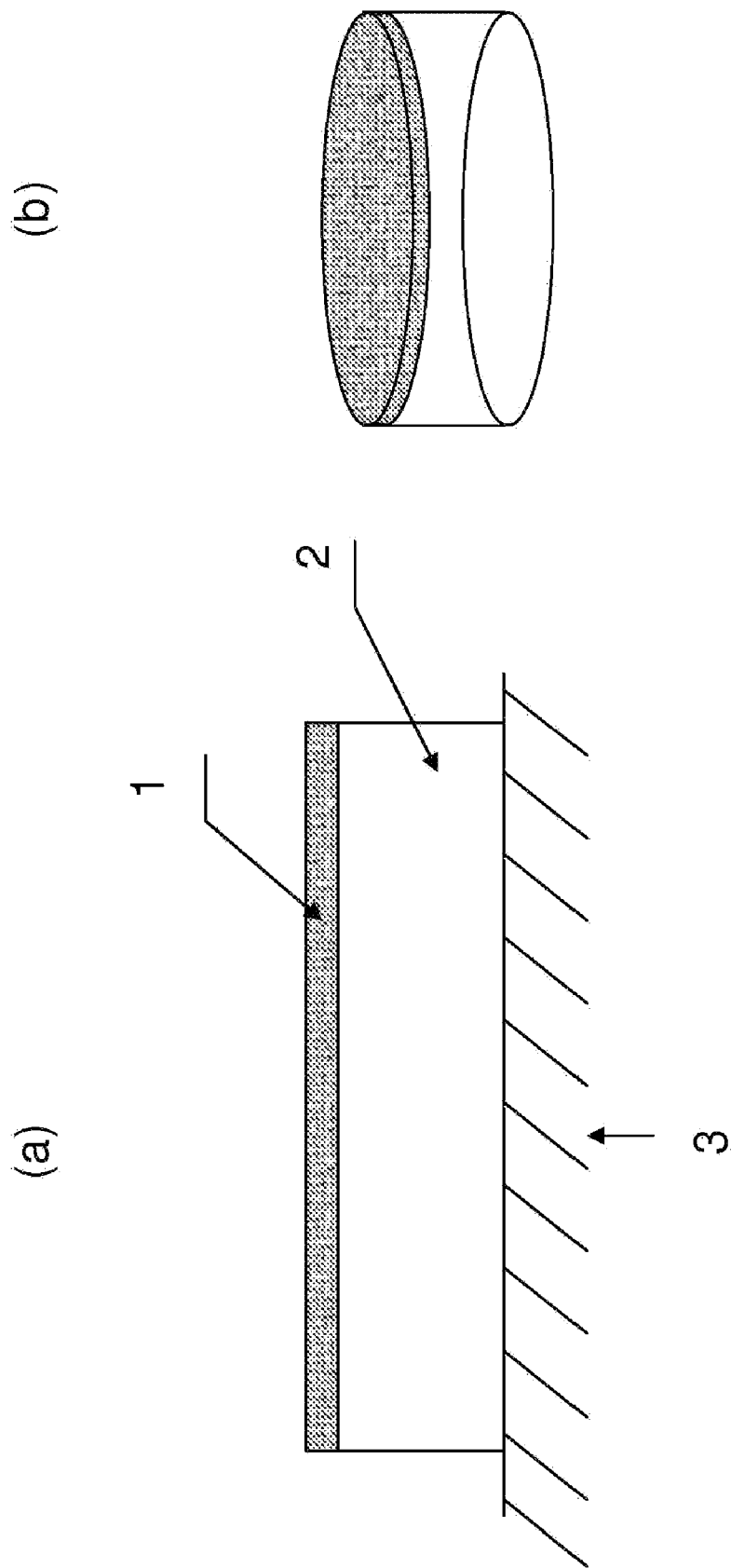
FIG. 1A and 1B illustrate an example organic sensor device.

Some example embodiments of the present invention generally relate to an organic sensor device sensitive to changes in pressure, tension, deformation, gases and/or temperature in the fields of molecular electronics or plastic electronics. The organic sensor device may include a layer of organic material in close contact with a base substrate. However, at present there is a growing need to manufacture gas, temperature and pressure sensors at low costs and with additional features. This requires the use of fewer components and manufacturing processes and the discovery of cheaper or new materials. Additionally, for some applications, size and weight limitations can also be of great importance.

One of the main difficulties in designing and manufacturing polymer-based sensors is producing the electrical contacts with polymeric materials. Microelectronic techniques allow manufacturing of high-precision electrodes; nevertheless, the techniques used give rise to electrical contacts with resistances comparable to, or greater than, the intrinsic resistance of a polymer, which leads to inaccurate measurements. Additionally, difficulty with polymeric sensors is a result of the fact that the resistance temperature coefficients (CTR) of many polymers are very high and, consequently, it is often necessary to use temperature compensation techniques that increase final sensor cost.

Further still, another difficulty of these devices is that the polymers are normally synthesized by electrochemical means. Therefore, it is necessary to use electrochemical equipment and manufacture metallic electrodes, typically made of gold or platinum. The adhesion of polymers to the substrate can also be a problem, in addition to the area of the device being limited by the separation of the electrodes. Additionally, the polymeric organic sensors tend to become easily degraded.

Therefore, there is a need to find new accurate and low-cost organic sensors. Among molecular conductive materials, transfer salt crystals are highly promising because their conductivity at ambient temperature is very sensitive to pressure changes and their conductivity typically increases linearly with temperature. Most of these molecular crystals are metals or semiconductors with very low activation energy and, therefore, their CTRs are lower than those of the organic polymers. Organic conductors are softer than metals and inorganic semiconductors and, therefore, the piezoresistivity values of molecular conductors are greater than those of traditional conductors. For example, at 8 Kbar the conductivity of the molecular superconductor β-$(ET)_2I_3$ [ET=bis(ethylenedithio)tetrathiafulvalene] is an order of magnitude greater than at ambient pressure.

The conductivity in conductive organic salt crystals, typically based on tetrathiafulvalene derivatives, have different types of response to temperature. However, the sensory properties of molecular crystals do not translate into immediate applications. The fragility of molecular crystals makes them inadequate for the manufacture of electronic devices and, consequently, alternative solutions must be found.

Described herein are organic sensor devices being low in cost and having high processability and flexibility, low weight and the possibility of modulating their properties by means of chemical synthesis.

The use of molecular conductor-based sensors eliminates many of the problems associated with polymer-based organic sensors, as the layer of molecular conductors can be prepared in any type of substrate, without using electrochemical methods.

The resistance of sensors prepared according to the present description reveals a high piezosensitivity effect within a pressure range of about 0 to about 100 mbar (K=45%), which can be of great interest to medical applications. Additionally, the data presented herein also reveals that the sensors are temperature-sensitive, especially within a temperature range of about 25° C. to about 65° C., which can be of great interest to medical and biomedical applications.

Generally, described herein are organic sensor devices including a layer of organic material wherein the organic layer is formed of at least one salt or conductive complex including a molecule A and a dopant D. Molecule A is an electron donor organic molecule, an electron acceptor organic molecule, a macromolecule capable of forming a conductive salt or macromolecule capable of forming a complex, which without doping is not conductive. Dopant D is a compound that is an electron acceptor or donor capable of forming a salt or conductive complex with molecule A.

The organic sensor devices further include a base substrate in close contact with the layer of organic material, wherein the base substrate is inert with respect to the layer of organic material. The organic sensor devices have the capacity to detect pressure changes resulting from a force applied directly on at least a part of the surface of the organic material, such as a tension, deformation, shearing or pressure exerted by a fluid and/or temperature changes.

Molecule A may be selected from an acene derivative, a coronene derivative, a tetrathiafulvalene derivative or tetracyanoquinodimethane derivative, preferring bis(ethylenthio)tetrathiafulvalene (BET-TTF) or bis(ethylendithio)tetrathiafulvalene (BEDT-TTF). On the other hand, dopant D may be a volatile species, being a volatile species selected from iodine, bromine, iodine bromide, chlorine or iodine chloride.

In one example embodiment, the salt is selected from among $(BEDT-TTF)_2I_3$ and $(BET-TTF)_2I_xBr_{3-x}$, where BET-TTF is bis(ethylenthio)tetrathiafulvalene and BEDT-TTF is bis(etylendithio)tetrathiafulvalene. In another example embodiment, the base substrate is inert with respect to the organic layer and sensitive to changes in pressure, tension, deformation, gases or temperature. The base substrate may be inorganic such as, for example, silicium oxide, silicone oxide or aluminum oxide, metallic, polymeric or a three-dimensional crystal.

In yet another example embodiment, the base substrate is a non-conductive organic polymer or a thermoplastic polymer or elastomer. Even further still, the base substrate is selected from polycarbonate, polymethylmetacrilate, polyethylene or polypropylene.

For example embodiments that are used as pressure sensors, the substrate has a high resistance to cyclic mechanical loading and is difficult to break under load application. Under load applications an organic layer sensitive to changes in pressure, deformation, tension or gases formed by a material with a high piezoresistivity and low temperature resistance coefficient is also preferable, with $(BEDT-TTF)_2I_3$ as the organic layer.

For example embodiments as a temperature sensor, the substrate is not be degraded as a consequence of temperature changes and the layer of organic material shall preferably be $(BET-TTF)_2I_xBr_{3-x}$.

Figure 2:
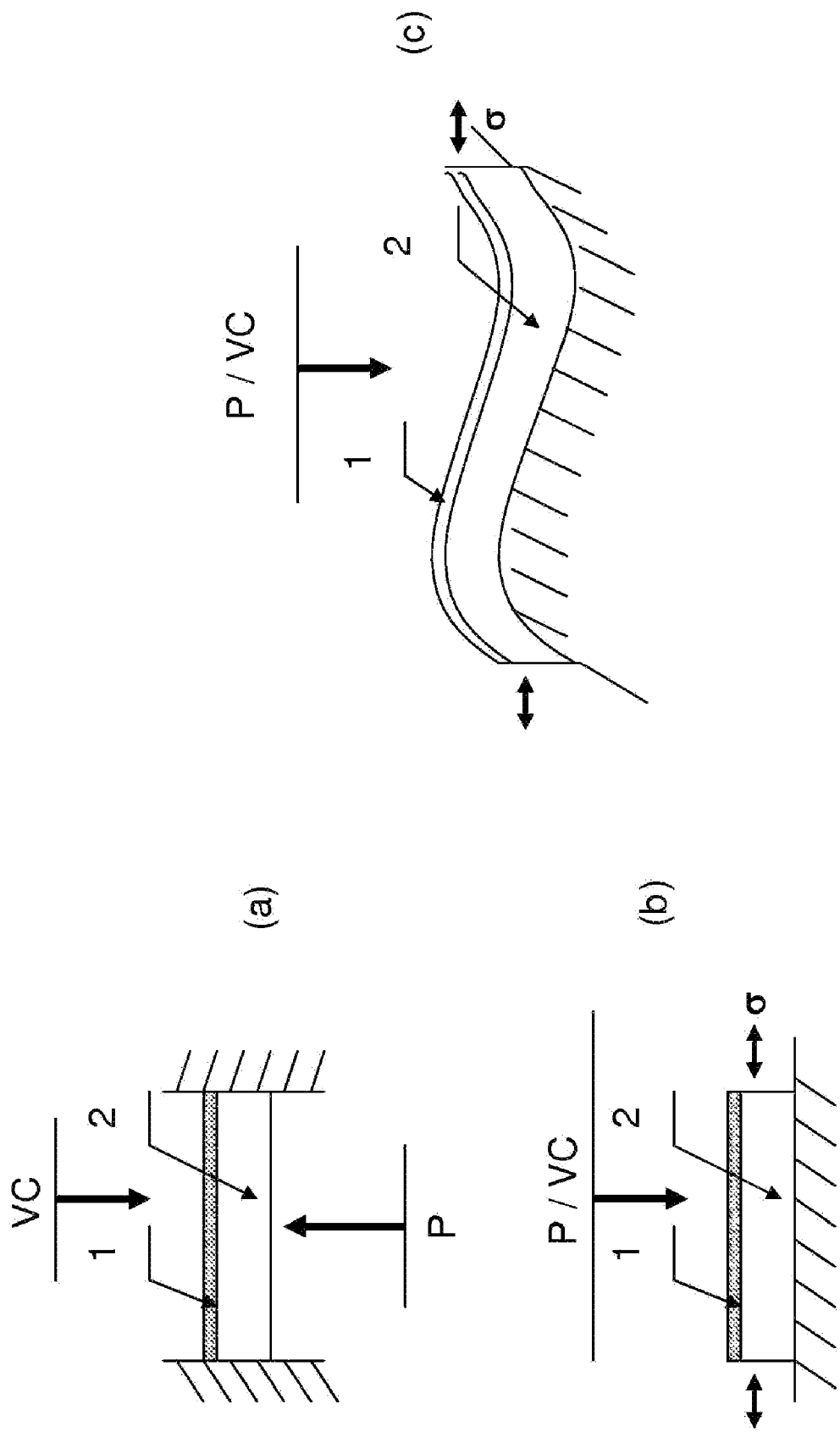
FIGS. 2A-C illustrate example embodiments wherein the organic sensor device has a diaphragm-type configuration.

Resulting is a layer of material of organic nature having different conductive surface properties that are modified by changes in temperature or through the application of pressure, tension or deformations. The shape, configuration or thickness of the sensory organic layer or substrate is not limited herein. In one example embodiment, a diaphragm-type configuration as illustrated in FIG. 2 shall be used. The resulting sensory organic layer acts as an electric signal sensing and transductive material.

FIG. 1 illustrates an example embodiment of the present description wherein an organic sensor device includes a layer of organic material 1, sensitive to changes in pressure, deformation or tension, in close contact with base substrate 2. Such a device is disposed on glass support 3.

FIGS. 2A-C illustrate example embodiments where the organic sensor device has a diaphragm-type configuration. The layer of organic material 1 acts as a sensor material (P=pressure, VC=volatile compounds, σ=tension) and as an electric signal transducer. In FIG. 2A, the organic sensor device is wedged between two materials; in FIG. 2B, the organic sensor device is placed atop a linear material; and in FIG. 2C, the organic sensor device is placed atop a non-linear material. All three placements are considered when utilizing the devices according to the present description.

Figure 4:
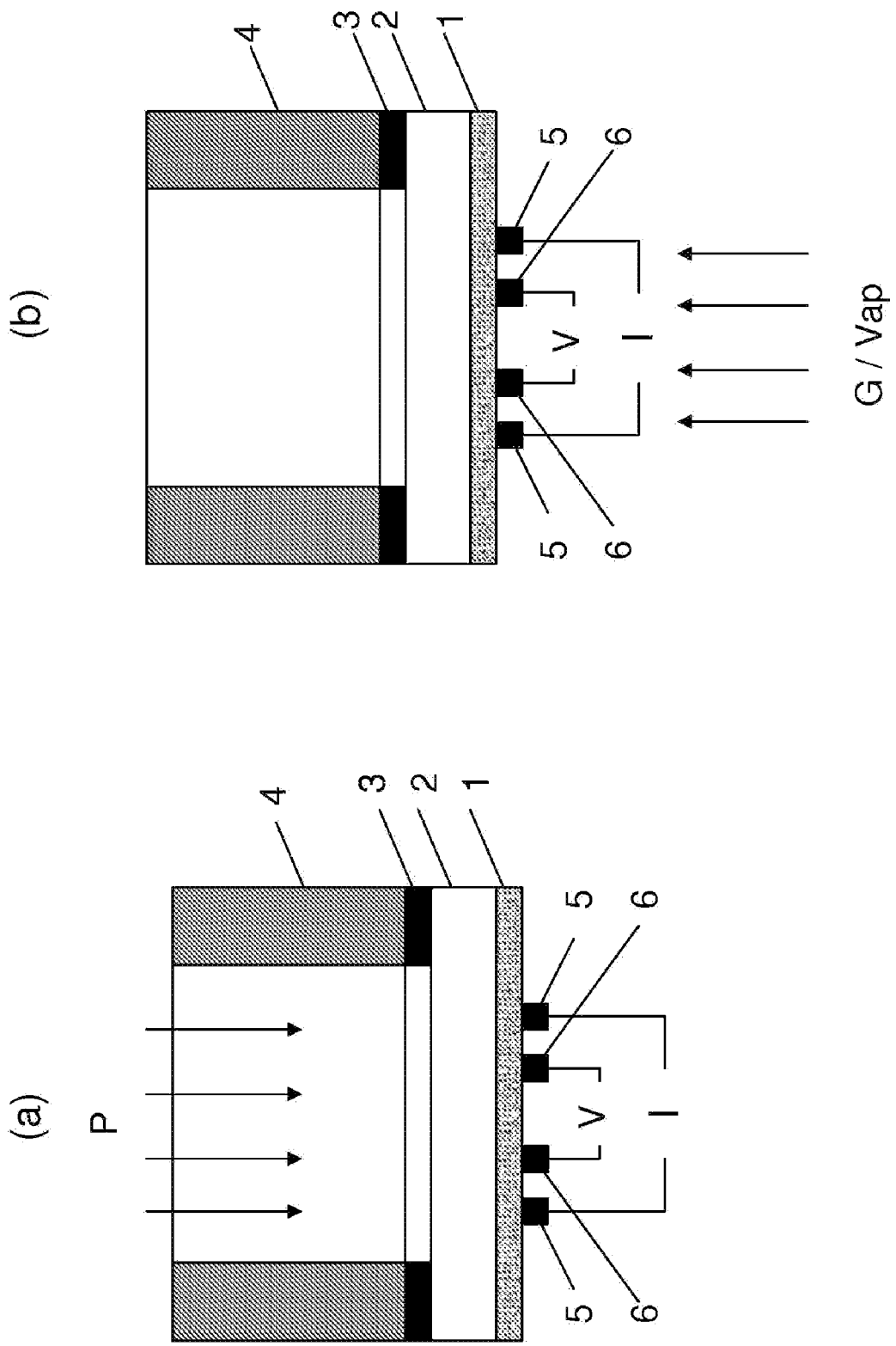
FIGS. 4A and 4B illustrate another example embodiment of an organic sensor device.

FIG. 4 illustrates another example embodiment of an organic sensor device including support 1, layer of organic material 2, epoxy resin 3, glass tube 4, two contacts for measuring the current 5, and two contacts for applying voltage 6. In the FIGS. 4A and 4B, (P) refers to pressure, (G) to gases and (Vap) to organic solvent vapors.

Figure 3:
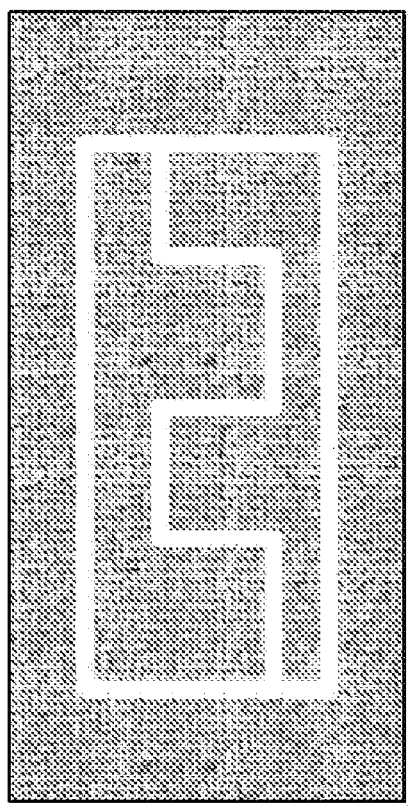
FIGS. 3A and 3B illustrate patterns designed in the same layer of sensory organic material.
Figure 3:
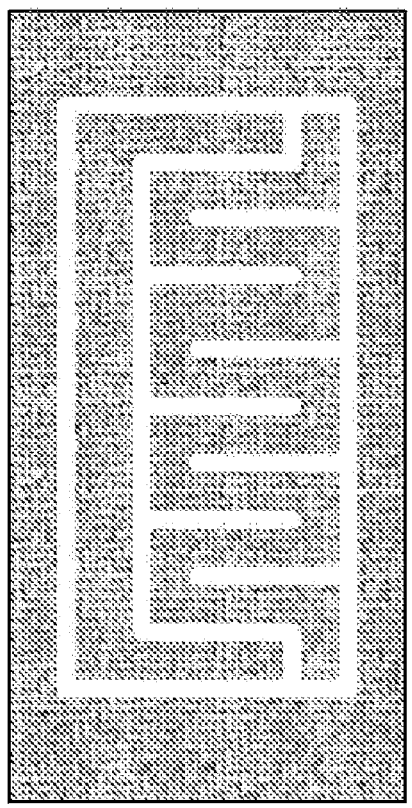

In order to transduce the data, patterns, circuits or devices (for example, resistors, condensers, transistors, etc.) can be designed in the same sensory organic layer (FIGS. 3A and B) using the techniques described in Patent Application ES/200501879 which is incorporated herein in its entirety for all it discloses regarding methods for obtaining patterns on a conductive organic layer. In this manner, the change-sensitive organic layer may also act as a circuit.

Patent Application ES 200501879 describes a method for obtaining patterns on a conductive organic layer consisting of: exposing a conductive organic layer to a heat source, where the conductive organic layer is formed of a salt or conductive complex including a molecule A and a dopant D, the molecule A being an electron donor or acceptor organic molecule or macromolecule capable of forming a conductive salt or complex, and the dopant D being an electron acceptor or donor, preferably volatile, capable of forming a salt or conductive complex with the molecule or macromolecule A.

The conductive organic layer is formed in such a manner that a thermal reaction takes place which modifies the chemical composition of the organic layer, leaving areas exempt from dopant D in accordance with the following reaction:

$$A_xD \xrightarrow{\Delta} x\ A\ +\ D.$$

Optionally, the heat source can be applied locally to the conductive organic layer following a pattern designed at millimetric, micrometric or nanometric scale, or in general over the whole surface through the use of thermally insulating intermediate masks having the specific previously designed pattern. Further, a mask can also be used on the organic layer that is heated, in such a manner that the thermal reaction takes place on the part of the mask in contact with the organic layer.

However, other types of electric contacts may also be used. In such an example embodiment, the organic layer, sensitive to changes in pressure and temperature, can be formed of crystals, fibers or other structures. The structure or morphology of the layer does not form part of the sensors described here, although, the layers formed by nanocrystals can be interesting for obtaining transparency and flexibility. The sensory organic layer may also contain metallic or conductive particles or other additive compounds.

Providing a method for obtaining the sensory organic layer over a base substrate does not form part of the sensors described herein. However, the methods described in Patent EP 19840109489, 19840809 or in E. Laukhina et al. Synthetic Metals 70 (1995) 795 shall be used, because it is a very simple and inexpensive method that allows the sensory organic layer to be prepared directly over a polymeric base substrate. The sensory organic layer may also be prepared by other methods, such as by direct evaporation of the salt or AD complex or of the precursor A and D compounds on the base substrate, directly giving rise to the sensory organic layer formed by the salt or AD complex.

The organic sensor device can be manufactured in polymeric substrates, giving rise to a flexible device that is completely organic, low in weight and transparent. Further, the organic sensor device may be manufactured at different scales, including at micro- and nanometric scale. In one example embodiment, the organic sensor device may be highly sensitive to changes in pressure, tension, deformation and/or temperature.

Further, the organic material defined in the organic layer of the organic sensor devices described herein can be used as sensor elements for detecting changes in pressure, tension, deformation or temperature, regardless of the presence or non-presence of other elements such as a base substrate.

Further still, the sensor device is of application in molecular electronics or plastic electronics and, in particular, in the field of organic sensors. The sensor devices described herein are of special interest in breathing masks, medicine in general, motoring, clothes, textiles, intelligent footwear, and the like.

EXAMPLE 1

Pressure Sensing Device Formed of a Layer of $(BEDT\text{-}TTF)_2I_3$ [BEDT-TTF: bis(ethylendithio-tetrathiafulvalene)] over Polycarbonate A mixture of 0.98 g of poly-(bisphenol-A-carbonate) (PC) and 0.02 g of bis(ethylendithio)-tetrathiafulvalene (BEDT-TTF) was prepared in 50 mL of 1,2-dichlorobenzene and heated at 80° C. until the total dissolution thereof. The resulting solution was deposited on a glass surface at 130° C., allowing the solvent to evaporate, thereby obtaining a film having a thickness of 20 microns. Next, the film surface was exposed to the vapors of a dissolution saturated with iodine in methylene chloride for three minutes. The result was the formation of a semiconductive superficial layer having a thickness of 1.5 microns formed by $(BEDT\text{-}TTF)_2I_3$ salt micro- and nanocrystals.

Figure 5:
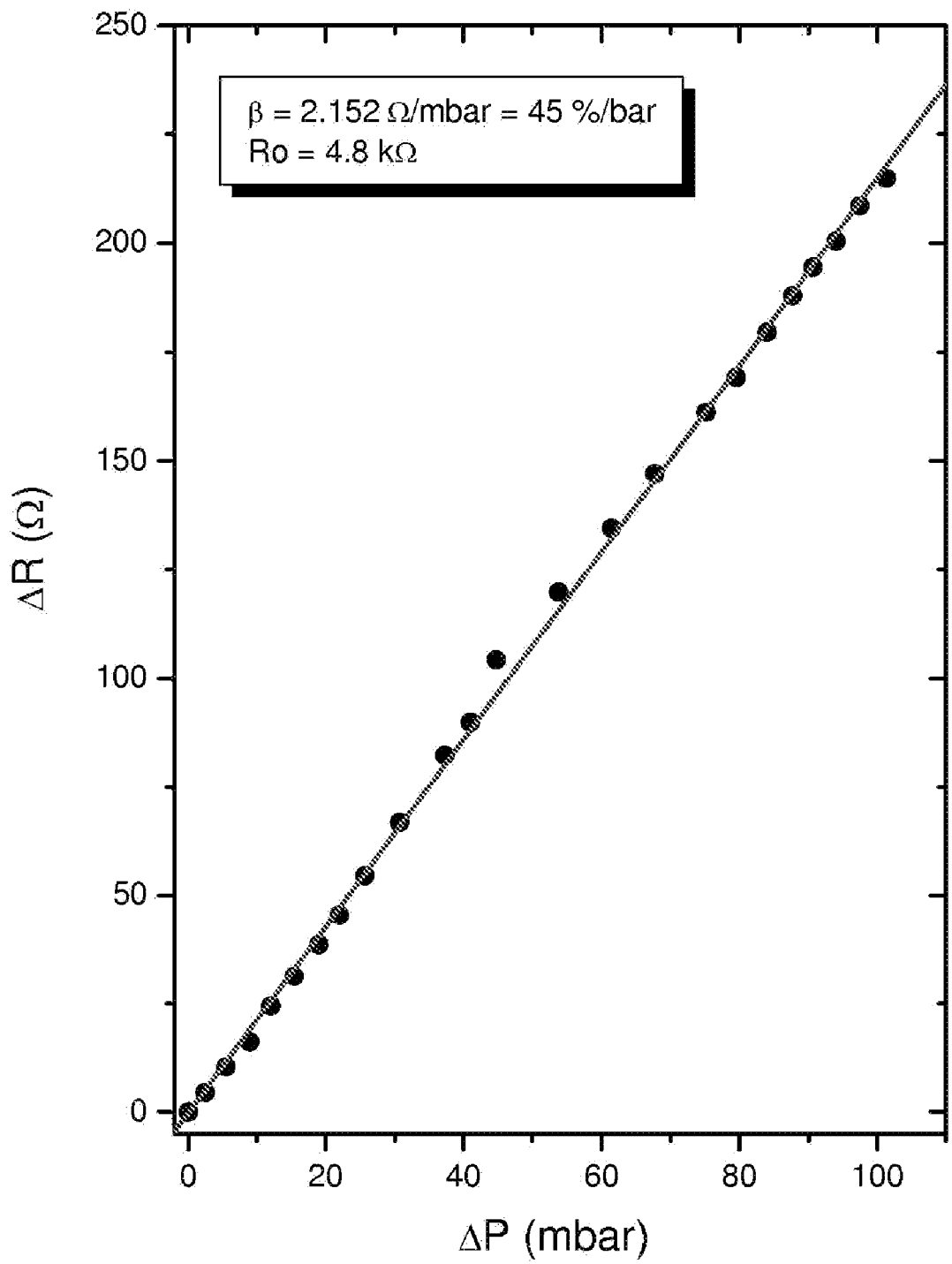
FIG. 5 graphically illustrates the dependence of the resistor with the pressure applied in an organic sensor device formed of $(BEDT-TTF)_2I_3$ and polycarbonate at an ambient temperature of 35° C. as well as the high piezoelectric effect of the organic sensor device.

The film was cut into a circular sample having a diameter of 8 mm (resistance to ambient conditions of 4.8 kOhm) and mounted on a glass tube with epoxy. The dependence of the resistance with pressure was measured using the four-point dc method with four platinum cables having a diameter of 20 microns (FIG. 4). The resistance of the film demonstrates a high piezoelectric effect (FIG. 5). Within a pressure range of 0-100 mbar, resistance increased linearly at a speed of 45% $bar^{-1}$.

EXAMPLE 2

Gas Sensing Device Formed of a Layer of $(BET\text{-}TTF)_2I_xBr_{3-x}$ [BET-TTF: bis(ethylenthio-tetrathiafulvalene)] over Polycarbonate A mixture of 0.98 g of poly-(bisphenol-A-carbonate) (PC) and 0.02 g of bis(ethylenthio)-tetrathiafulvalene (BET-TTF) was prepared in 50 mL of 1,2-dichlorobenzene and heated at 80° C. until the total dissolution thereof. The resulting solution was deposited on a glass surface at 130° C., allowing the solvent to evaporate, thereby obtaining a film having a thickness of 25 microns.

I. The surface of the film was exposed to the vapors of a dissolution saturated with iodine bromide in methylene chloride for five minutes. The result was the formation of a semiconductive superficial layer having a thickness of 1.5 microns formed by $(BET\text{-}TTF)_2I_xBr_{3-x}$ salt micro- and nanocrystals.

Figure 6:
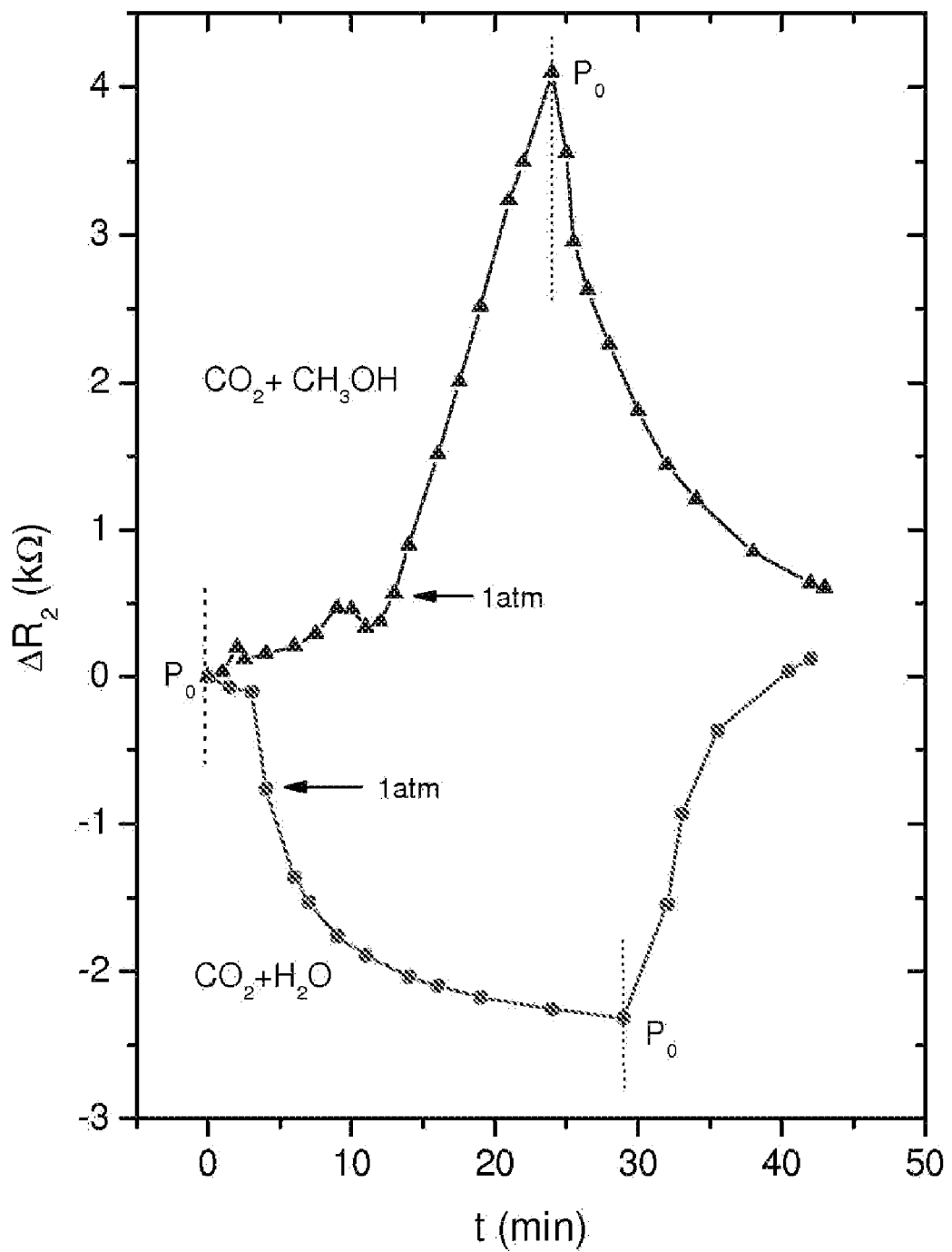
FIG. 6 graphically illustrates the response of an organic sensor device according to still another example embodiment. Plotted are the variation in the resistance of an organic sensor device formed of $(BEDT-TTF)_2I_3$ and polycarbonate in a vacuum ($P_0$) and in the presence of a combination of gases: $CO_2$ with methanol and $CO_2$ with water.

The film was cut into a circular sample having a diameter of 10 mm (resistance to ambient conditions of 4.3 kOhm) and mounted on a glass tube with epoxy. In order to activate the gas-sensing properties, the sensor was placed in a vacuum chamber to eliminate the possible gases or impurities that could be absorbed in the film. The dependence of the resistance with the presence of a $CO_2$-bearing gas that contained water or methanol was measured using the four-point dc method with four platinum cables having a diameter of 20 microns (FIG. 4). The response of the sensor is graphically illustrated in FIG. 6, where it can be seen that the sensor is very sensitive and responds to the two gas mixtures in a selective manner: resistance increases significantly when the $CO_2$ contains methanol and diminishes when it contains water. Upon producing a vacuum the initial value of the resistance is recovered.

II. The film surface was exposed to the vapors of a dissolution saturated with iodine bromide in methylene chloride for six minutes. The result was the formation of a semiconductive superficial layer having a thickness of 1.5 microns formed of $(BET\text{-}TTF)_2I_xBr_{3-x}$ salt micro- and nanocrystals.

Figure 7:
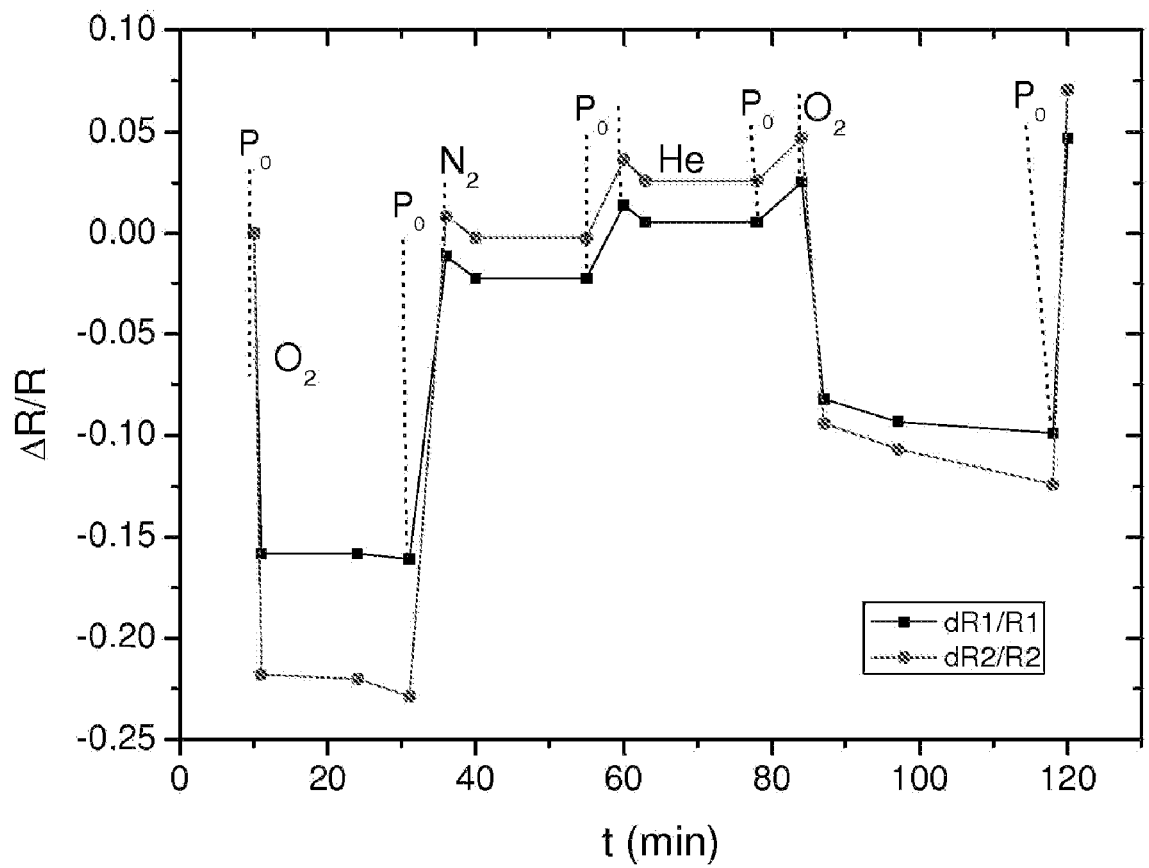
FIG. 7 graphically illustrates the response of a sensory organic material according to another example embodiment. Plotted are the variation in the resistance of an organic sensor formed of $(BEDT-TTF)_2I_3$ and polycarbonate in a vacuum ($P_0$), and in the presence of $O_2$, $N_2$ and He.

The film was cut into a circular sample having a diameter of 10 mm (resistance to ambient conditions of 3.0 kOhm) and mounted on a glass tube with epoxy. In order to activate the gas-sensing properties, the sensor was placed in a vacuum chamber to eliminate the possible gases or impurities that could be absorbed in the film. The film was exposed to $O_2$, $N_2$ and He gases and the electric response was measured using the four-point dc method with four platinum cables having a diameter of 20 microns. The response of the sensor device is graphically illustrated in FIG. 7, where it can be seen that the sensor reacts differently to the presence of these gases: in a vacuum, $N_2$ or He atmosphere the resistance of the organic conductor increases with respect to the resistance in an $O_2$ atmosphere. After producing the vacuum, the initial value of the resistance is recovered.

III. The film surface was exposed to the vapors of a dissolution saturated with iodine bromide in methylene chloride for eight minutes. The result was the formation of a semiconductive superficial layer having a thickness of 2 microns formed of $(BET\text{-}TTF)_2I_xBr_{3-x}$ salt micro- and nanocrystals.

The film was cut into a circular sample having a diameter of 10 mm (resistance to ambient conditions of 2.6 kOhm) and mounted on a glass tube with epoxy. In order to activate the gas-sensing properties, the sensor was placed in a vacuum chamber to eliminate the possible gases or impurities that could be absorbed in the film. The film was exposed to $O_2$, $N_2$ and He gases and the electric response was measured using the four-point dc method with four platinum cables having a diameter of 20 microns. The response of the sensor device is graphically illustrated in FIG. 7, where it can be seen that the film is very sensitive to the gases to which it is exposed, although the response is lower than in the case of the film described in Example 2b. After producing the vacuum, the initial value of the resistance was recovered.

IV. The film surface was exposed to the vapors of a dissolution of 1 mg/mL of iodine bromide in methylene chloride for two minutes. The result was the formation of a semiconductive superficial layer having a thickness of 1.5 microns formed of $(BET\text{-}TTF)_2I_xBr_{3-x}$ salt micro- and nanocrystals.

Figure 8:
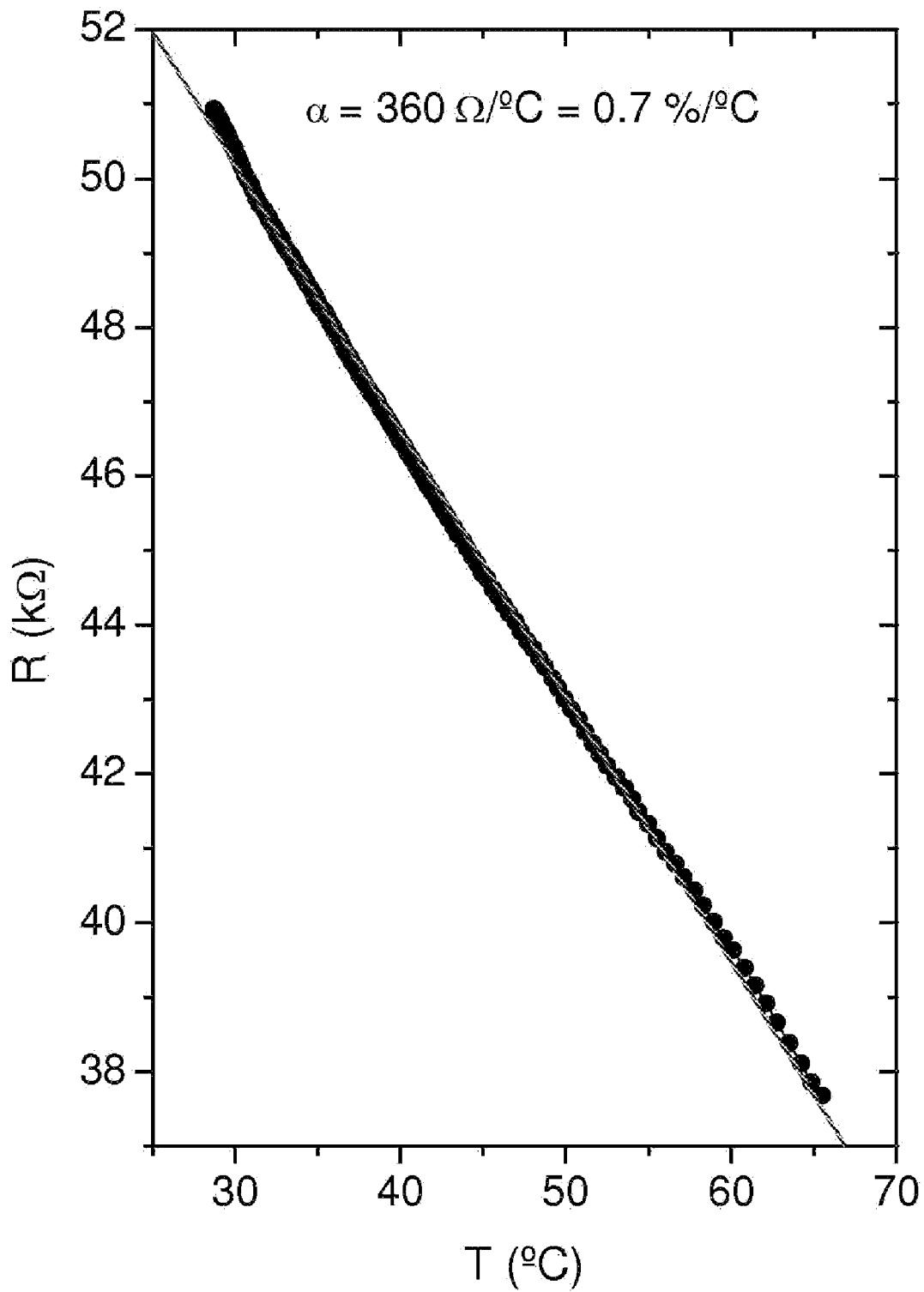
FIG. 8 graphically illustrates the response of a sensory organic material according to yet another example embodiment. Plotted are the variation, at ambient pressure, of the resistance with the temperature applied in an organic sensor device formed of $(BET-TTF)_2I_xBr_{3-x}$ and polycarbonate.

A $2\times1$ mm$^2$ rectangular sample of the film was cut and the dependence of the resistance with the temperature was measured using the four-point dc method with four platinum cables having a diameter of 20 microns. The resistance of the film reveals a high effect with the temperature (FIG. 8). Within a temperature range of 28-65° C. resistance diminishes linearly at a speed of 7% ° C$^{-1}$.

EXAMPLE 3

Parameters of Organic Sensors

Results (see Table 1, Table 2 and Table 3) of trials conducted on an organic sensor device in accordance with the present invention are included below.

TABLE 1

| N | $\Delta P$ (mbar) | $\Delta R$ (Ohm) | $\Delta R/R_0$ (%) |
|---|---|---|---|
| 1 | 0 | 0 | 0 |
| 2 | 2.5 | 4.5 | 0.09 |
| 3 | 5.5 | 10.4 | 0.22 |
| 4 | 9.0 | 16.2 | 0.34 |
| 5 | 12.0 | 24.4 | 0.51 |
| 6 | 15.4 | 31.3 | 0.65 |
| 7 | 19.0 | 38.7 | 0.80 |
| 8 | 22.0 | 45.5 | 0.95 |
| 9 | 25.7 | 54.5 | 1.14 |
| 10 | 30.7 | 66.9 | 1.39 |
| 11 | 37.3 | 82.3 | 1.71 |
| 12 | 41.0 | 89.9 | 1.87 |
| 13 | 44.8 | 104.2 | 2.17 |
| 14 | 53.8 | 119.9 | 2.50 |
| 15 | 61.5 | 134.6 | 2.80 |
| 16 | 67.7 | 147.1 | 3.06 |
| 17 | 75.1 | 161.2 | 3.36 |
| 18 | 79.5 | 169.2 | 3.51 |
| 19 | 84.0 | 179.6 | 3.74 |
| 20 | 87.7 | 187.9 | 3.91 |
| 21 | 90.6 | 194.4 | 4.05 |
| 22 | 94.0 | 200.4 | 4.18 |
| 23 | 97.5 | 208.6 | 4.35 |
| 24 | 101.3 | 214.9 | 4.48 |
| 25 | 93.9 | 207.5 | 4.32 |
| 26 | 90.0 | 200.6 | 4.18 |
| 27 | 86.0 | 193.0 | 4.02 |
| 28 | 82.2 | 183.5 | 3.82 |
| 29 | 77.8 | 176.1 | 3.66 |
| 30 | 70.1 | 161.4 | 3.36 |
| 31 | 52.5 | 123.9 | 2.58 |
| 32 | 27.0 | 67.7 | 1.41 |
| 33 | 20.6 | 54.3 | 1.13 |
| 34 | 13.0 | 34.3 | 0.71 |
| 35 | 0 | 0 | 0 |

Piezosensitivity $\kappa = \Delta R/\Delta P\, R_0$; $\kappa \approx 45\%$

Table 1 shows the results obtained in a sensor device based on a layer of organic material $(BEDT\text{-}TTF)_2I_3$, where $\Delta P=P-P_0$ is the pressure differential between the applied pressure P and the ambient pressure $P_0$; and where $\Delta R=R(P)-R_0$ is the resistance differential between the resistance to an applied pressure $R(P)$ and the resistance to the ambient pressure $R_0$.

TABLE 2

| Gas | $\Delta R/R_0$ |
|---|---|
| Nitrogen | −0.01 |
| Helium | −0.01 |
| $CO_2$ | 0.01 |
| $CO_2 + H_2O$ | −0.13 |
| $CO_2 + CH_3OH$ | 0.23 |
| Oxygen | −0.22 |

Table 2 shows results on the sensitivity of the gases of the resistance of the layer of sensor organic material to gas changes in a sensor device based on the molecular conductor $(BET\text{-}TTF)_2I_xBr_{3-x}$ where $\Delta R=R(gas)-R_0$ is the resistance differential between the resistance of layer i) in the presence of a gas and the resistance $R_0$ of the layer i) in a vacuum ($R_0=18$ kOhm).

TABLE 3

| N | T (° C.) | R(T) (kΩ) | $\Delta R$ (kΩ) | $\Delta R/R_0$ (%) |
|---|---|---|---|---|
| 1 | 28.000 | 51.164 | 0 | 0 |
| 2 | 29.276 | 50.681 | −0.483 | −0.94 |
| 3 | 30.552 | 50.083 | −1.081 | −2.11 |
| 4 | 31.828 | 49.559 | −1.605 | −3.14 |
| 5 | 33.103 | 49.059 | −2.105 | −4.11 |
| 6 | 34.379 | 48.587 | −2.577 | −5.04 |
| 7 | 35.655 | 48.111 | −3.053 | −5.97 |
| 8 | 36.931 | 47.607 | −3.557 | −6.95 |
| 9 | 38.207 | 47.119 | −4.045 | −7.91 |
| 10 | 39.483 | 46.665 | −4.499 | −8.79 |
| 11 | 40.759 | 46.206 | −4.958 | −9.69 |
| 12 | 42.034 | 45.747 | −5.417 | −10.59 |
| 13 | 43.310 | 45.287 | −5.877 | −11.49 |
| 14 | 44.586 | 44.848 | −6.316 | −12.34 |
| 15 | 45.862 | 44.401 | −6.763 | −13.22 |
| 16 | 47.138 | 43.980 | −7.184 | −14.04 |
| 17 | 48.414 | 43.547 | −7.617 | −14.89 |
| 18 | 49.690 | 43.106 | −8.058 | −15.75 |
| 19 | 50.966 | 42.660 | −8.504 | −16.62 |
| 20 | 52.241 | 42.212 | −8.952 | −17.50 |
| 21 | 53.517 | 41.826 | −9.338 | −18.25 |
| 22 | 54.793 | 41.379 | −9.785 | −19.13 |
| 23 | 56.069 | 40.938 | −10.226 | −19.99 |
| 24 | 57.345 | 40.551 | −10.613 | −20.74 |
| 25 | 58.621 | 40.118 | −11.046 | −21.59 |
| 26 | 59.897 | 39.691 | −11.473 | −22.42 |
| 27 | 61.172 | 39.258 | −11.906 | −23.27 |
| 28 | 62.448 | 38.788 | −12.376 | −24.19 |
| 29 | 63.724 | 38.297 | −12.867 | −25.15 |
| 30 | 65.000 | 37.820 | −13.344 | −26.08 |

Table 3 shows results obtained in a sensor device based on a layer of organic material $(BET)_2I_xBr_{3-x}$, where $\Delta R=R(T)-R_0$ is the resistance differential between resistance at an applied temperature and resistance at ambient temperature.

The invention claimed is:

1. An organic sensor device comprising:
   i) an organic layer comprising at least one salt or conductive complex including a molecule A and a dopant D, wherein said molecule A is selected from a coronene derivative, a tetrahiafulvalene derivative or a tetracyanoquinodimethane derivative, which without doping is not conductive, and wherein said dopant D is an electron acceptor or an electron donor capable of forming a salt or conductive complex with the molecule A; and ii) a non-conducting base substrate in close contact with said organic layer, wherein said base substrate is inert with respect to said organic layer, and
wherein said organic layer is sensitive to a change in pressure, tension, deformation, or temperature.

2. The organic sensor device according to claim 1, wherein said molecule A is selected from bis(ethylenthio)tetrathiafulvalene (BET-TTF) or bis(etylendithio)tetrathiafulvalene (BEDT-TTF).

3. The organic sensor device according to claim 1, wherein said dopant D is a volatile species.

4. The organic sensor device according to claim 3, wherein said volatile species is selected from iodine, bromine, iodine bromide, chlorine or iodine chloride.

5. The organic sensor device according to claim 1, wherein said at least one salt is selected from $(BEDT-TTF)_2I_3$ and $(BET-TTF)_2I_xBr_{3-x}$, wherein BET-TTF is bis(ethylenthio)tetrathiafulvalene and BEDT-TTF is bis(etylendithio)tetrathiafulvalene.

6. The organic sensor device according to claim 1, wherein said base substrate is inorganic polymeric or a three-dimensional crystal.

7. The organic sensor device according to claim 6, wherein said base substrate is silicone oxide or aluminium oxide.

8. The organic sensor device according to claim 6, wherein said base substrate is a non-conductive organic polymer.

9. The organic sensor device according to claim 8, wherein said base substrate is a thermoplastic polymer or elastomer.

10. The organic sensor device according to claim 9, wherein said base substrate is selected from polycarbonate, polymethylmetacrilate, polyethylene or polypropylene.

11. The organic sensor device according to claim 1, wherein said organic layer is $(BEDT-TTF)_2I_3$ and wherein said organic sensor device is functional as a pressure sensor, a tension sensor or a deformation sensor.

12. The organic sensor device according to claim 1, wherein said organic layer is $(BEDT-TTF)_2I_xBr_{3-x}$ and wherein said organic sensor device is functional as a temperature sensor.

13. The organic sensor device according to claim 1, wherein said changes in pressure or temperature produce a linear response in the resistance of the device.

14. The organic sensor device according to claim 12, wherein said temperature sensor is functional within a temperature range of about 25° C. to about 65° C.

15. The organic sensor device according to claim 1, wherein said organic sensor device detects a force applied on at least a part of said organic layer, wherein said force is a deformation, a shearing, a tension or a pressure.

16. The organic sensor device according to claim 15, wherein pressure is exerted by a pressure change or a temperature change.

17. The organic sensor device according to claim 1, wherein said organic layer is $(BEDT-TTF)_2I_3$ and wherein said organic sensor device is functional as a strain sensor.

18. An organic pressure, tension, deformation, or temperature sensor comprising:
iii) an organic layer comprising a salt or conductive complex including a molecule A and a dopant D, wherein said molecule A is selected from a coronene derivative, a tetrahiafulvalene derivative or a tetracyanoquinodimethane, and wherein said dopant D is an electron acceptor or an electron donor; and
iv) a non-conducting base substrate in close contact with said organic layer, wherein said base substrate is inert with respect to said organic layer, and
wherein said sensor is configured to detect changes in pressure due to a force applied to at least a portion of the organic layer.

* * * * *